(12) United States Patent
Hilton et al.

(10) Patent No.: US 8,709,112 B2
(45) Date of Patent: Apr. 29, 2014

(54) SYSTEMS AND METHODS FOR QUENCHING, GAS CLEAN UP, AND ASH REMOVAL

(75) Inventors: Courtland Hilton, Broomfield, CO (US); Zoran Jovanovic, Louisville, CO (US); Bryan Schramm, Broomfield, CO (US); Christopher Perkins, Boulder, CO (US); Wayne Simmons, Dublin, OH (US)

(73) Assignee: Sundrop Fuels, Inc., Longmont, CO (US)

( * ) Notice: Subject to any disclaimer, the term of this patent is extended or adjusted under 35 U.S.C. 154(b) by 980 days.

(21) Appl. No.: 12/796,319

(22) Filed: Jun. 8, 2010

(65) Prior Publication Data

US 2010/0243961 A1  Sep. 30, 2010

Related U.S. Application Data

(60) Provisional application No. 61/248,282, filed on Oct. 2, 2009, provisional application No. 61/185,492, filed on Jun. 9, 2009.

(51) Int. Cl.
  *C10J 3/08* (2006.01)
(52) U.S. Cl.
  USPC .......................................................... 48/62 R
(58) Field of Classification Search
  None
  See application file for complete search history.

(56) References Cited

U.S. PATENT DOCUMENTS

| | | |
|---|---|---|
| 1,508,464 A | 9/1924 | McFarland |
| 3,993,458 A * | 11/1976 | Antal, Jr. .................. 48/209 |
| 4,164,123 A | 8/1979 | Smith |
| 4,219,492 A | 8/1980 | Konoki et al. |
| 4,247,755 A | 1/1981 | Smith, Jr. et al. |
| 4,290,779 A * | 9/1981 | Frosch et al. ................ 422/186 |
| 4,415,339 A | 11/1983 | Aiman et al. |
| 4,455,153 A | 6/1984 | Jakahi |

(Continued)

FOREIGN PATENT DOCUMENTS

| | | |
|---|---|---|
| JP | 2002/012877 A | 1/2002 |
| SU | 1763814 A1 | 9/1992 |
| WO | WO 2010/144540 A1 | 12/2010 |
| WO | WO 2010/144544 A1 | 12/2010 |

OTHER PUBLICATIONS

Notice of Allowance for U.S. Appl. No. 12/796,121 mailed Oct. 11, 2012, 7 pages. U.S. Patent and Trademark Office, Alexandria, Virginia USA.

(Continued)

*Primary Examiner* — Imran Akram
(74) *Attorney, Agent, or Firm* — Rutan & Tucker, LLP

(57) ABSTRACT

A method, apparatus, and system for a solar-driven chemical plant are disclosed. An embodiment may include a solar thermal receiver aligned to absorb concentrated solar energy from one or more solar energy concentrating fields. A solar driven chemical reactor may include multiple reactor tubes located inside the solar thermal receiver. The multiple reactor tubes can be used to gasify particles of biomass in the presence of a carrier gas. The gasification reaction may produce reaction products that include hydrogen and carbon monoxide gas having an exit temperature from the tubes exceeding 1000 degrees C. An embodiment can include a quench zone immediately downstream of an exit of the chemical reactor. The quench zone may immediately quench via rapid cooling of at least the hydrogen and carbon monoxide reaction products within 0.1-10 seconds of exiting the chemical reactor to a temperature of 800 degrees C. or less.

16 Claims, 5 Drawing Sheets

(56) References Cited

U.S. PATENT DOCUMENTS

| | | | |
|---|---|---|---|
| 4,552,741 A | 11/1985 | Melchior | |
| 4,582,590 A * | 4/1986 | Qader | 208/409 |
| 4,704,137 A | 11/1987 | Richter | |
| 4,756,722 A | 7/1988 | Knop et al. | |
| 4,766,154 A | 8/1988 | Bonnell et al. | |
| 4,881,947 A * | 11/1989 | Parker et al. | 48/89 |
| 5,154,597 A * | 10/1992 | Fullemann et al. | 431/116 |
| 5,179,129 A | 1/1993 | Studer | |
| 5,496,859 A * | 3/1996 | Fong et al. | 518/703 |
| 5,581,998 A | 12/1996 | Craig | |
| 5,618,500 A | 4/1997 | Wang | |
| 5,647,877 A | 7/1997 | Epstein | |
| 5,906,799 A | 5/1999 | Burgie et al. | |
| 6,660,244 B2 | 12/2003 | Negishi et al. | |
| 6,676,716 B2 | 1/2004 | Fujimura et al. | |
| 6,872,378 B2 | 3/2005 | Weimer et al. | |
| 7,033,570 B2 | 4/2006 | Weimer et al. | |
| 7,207,327 B2 | 4/2007 | Litwin et al. | |
| 7,553,476 B2 | 6/2009 | Marrella et al. | |
| 7,632,476 B2 | 12/2009 | Shah et al. | |
| 7,686,856 B2 | 3/2010 | Hemmings et al. | |
| 7,856,829 B2 | 12/2010 | Shah et al. | |
| 7,871,457 B2 | 1/2011 | Shah et al. | |
| 7,881,825 B2 | 2/2011 | Esposito et al. | |
| 7,931,888 B2 | 4/2011 | Drnevich et al. | |
| 7,985,399 B2 | 7/2011 | Drnevich et al. | |
| 8,007,761 B2 | 8/2011 | Drnevich et al. | |
| 8,257,454 B1 * | 9/2012 | Haueter et al. | 48/210 |
| 8,378,151 B2 | 2/2013 | Perkins et al. | |
| 2002/0134019 A1 | 9/2002 | Paisley | |
| 2003/0182861 A1 * | 10/2003 | Weimer et al. | 48/197 R |
| 2003/0208959 A1 | 11/2003 | Weimer et al. | |
| 2003/0213514 A1 | 11/2003 | Ortabasi | |
| 2004/0170210 A1 | 9/2004 | Do et al. | |
| 2004/0219079 A1 | 11/2004 | Hagen et al. | |
| 2005/0020700 A1 | 1/2005 | Bahnisch | |
| 2005/0192362 A1 * | 9/2005 | Rodriguez et al. | 518/702 |
| 2006/0024538 A1 | 2/2006 | Steinberg | |
| 2006/0096298 A1 | 5/2006 | Barnicki et al. | |
| 2006/0140848 A1 | 6/2006 | Weimer et al. | |
| 2006/0188433 A1 | 8/2006 | Weimer et al. | |
| 2006/0225424 A1 | 10/2006 | Elliott et al. | |
| 2007/0098602 A1 | 5/2007 | Haueter et al. | |
| 2007/0129450 A1 | 6/2007 | Barnicki et al. | |
| 2007/0225382 A1 | 9/2007 | Van Den Berg et al. | |
| 2008/0057366 A1 | 3/2008 | Katikaneni et al. | |
| 2008/0086945 A1 * | 4/2008 | Wunning | 48/86 R |
| 2008/0086946 A1 | 4/2008 | Weimer et al. | |
| 2008/0104003 A1 | 5/2008 | Macharia et al. | |
| 2008/0209891 A1 | 9/2008 | Johannes et al. | |
| 2008/0223214 A1 | 9/2008 | Palamara et al. | |
| 2008/0284401 A1 | 11/2008 | Oettinger et al. | |
| 2008/0293132 A1 | 11/2008 | Goldman et al. | |
| 2008/0302670 A1 | 12/2008 | Boyle | |
| 2008/0307703 A1 | 12/2008 | Dietenberger | |
| 2009/0013601 A1 | 1/2009 | Mandich et al. | |
| 2009/0064578 A1 | 3/2009 | Theegala | |
| 2009/0093555 A1 | 4/2009 | Stites et al. | |
| 2009/0286295 A1 * | 11/2009 | Medoff et al. | 435/162 |
| 2009/0313886 A1 | 12/2009 | Hinman | |
| 2010/0000874 A1 | 1/2010 | Hinman | |
| 2010/0137459 A1 | 6/2010 | Stites et al. | |
| 2010/0219062 A1 * | 9/2010 | Leon Sanchez | 204/157.43 |
| 2010/0249468 A1 | 9/2010 | Perkins et al. | |
| 2010/0270505 A1 | 10/2010 | Gallaspy et al. | |
| 2010/0273899 A1 | 10/2010 | Winter | |
| 2010/0282131 A1 * | 11/2010 | Obrist et al. | 106/693 |
| 2011/0107661 A1 | 5/2011 | Tirmizi et al. | |
| 2011/0124927 A1 | 5/2011 | Stites et al. | |
| 2011/0155958 A1 | 6/2011 | Winter et al. | |

OTHER PUBLICATIONS

Non-Final Office Action for U.S. Appl. No. 12/796,121 mailed Jun. 7, 2012, 10 pages. U.S. Patent and Trademark Office, Alexandria, Virginia USA.

Written Opinion for International Application No. PCT/US2010/037914 mailed Aug. 13, 2010, 6 pages. International Searching Authority/US, Alexandria, Virginia USA.

Written Opinion for International Application No. PCT/US2010/037925 mailed Aug. 10, 2010, 8 pages. International Searching Authority/US, Alexandria, Virginia USA.

Cross Reference to Related Applications Under 27 C.F.R. 1.78, 2 pages.

International Search Report for PCT/US10/037911, dated Aug. 6, 2010, 2 pages.

International Search Report for PCT/US10/037914, dated Aug. 13, 2010, 2 pages.

International Search Report for PCT/US10/037923, dated Aug. 9, 2010, 3 pages.

International Search Report for PCT/US10/037925, dated Aug. 10, 2010, 3 pages.

International Search Report for PCT/US10/037930, dated Sep. 20, 2010, 5 pages.

International Search Report for PCT/US10/037934, dated Aug. 9, 2010, 2 pages.

International Search Report for PCT/US10/037938, dated Aug. 5, 2010, 2 pages.

International Search Report for PCT/US10/037940, dated Aug. 13, 2010, 2 pages.

International Search Report for PCT/US10/037944, dated Aug. 18, 2010, 2 pages.

Munzinger, M., et al., "Biomass Gass ification Using Solar Thermal Energy", *Anzses 2006*, pp. 1-10.

Mishra, Anuradha, et al., "Thermal Optimization of Solar Biomass Hybrid Cogeneration Plants", *Journal of Scientific & Industrial Research*, vol. 65, Apr. 2006, pp. 355-363.

Esser, Peter, et al., "The Photochemical Synthesis of Fine Chemicals With Sunlight," Angew. Chem. Int. Ed. Engl. 1994, vol. 33, pp. 2009-2023.

International Preliminary Report on Patentability for International Application No. PCT/US10/37911, dated Dec. 12, 2011, 9 pages.

International Preliminary Report on Patentability for International Application No. PCT/US10/37914, dated Dec. 12, 2011, 8 pages.

International Preliminary Report on Patentability for International Application No. PCT/US10/37923, dated Dec. 12, 2011, 13 pages.

International Preliminary Report on Patentability for International Application No. PCT/US10/37925, dated Dec. 12, 2011, 10 pages.

International Preliminary Report on Patentability for International Application No. PCT/US10/37930, dated Dec. 12, 2011, 13 pages.

International Preliminary Report on Patentability for International Application No. PCT/US10/37934, dated Dec. 12, 2011, 10 pages.

International Preliminary Report on Patentability for International Application No. PCT/US10/37938, dated Dec. 12, 2011, 10 pages.

International Preliminary Report on Patentability for International Application No. PCT/US10/37940, dated Dec. 12, 2011, 10 pages.

International Preliminary Report on Patentability for International Application No. PCT/US10/37944, dated Dec. 12, 2011, 10 pages.

* cited by examiner

SYSTEMS AND METHODS FOR QUENCHING, GAS CLEAN UP, AND ASH REMOVAL

RELATED APPLICATIONS

This application claims the benefit of both U.S. Provisional Patent Application Ser. No. 61/248,282, filed Oct. 2, 2009 and entitled "Various Methods and Apparatuses for Sun Driven Processes," and U.S. Provisional Patent Application Ser. No. 61/185,492, titled "VARIOUS METHODS AND APPARATUSES FOR SOLAR-THERMAL GASIFICATION OF BIOMASS TO PRODUCE SYNTHESIS GAS" filed Jun. 9, 2009.

NOTICE OF COPYRIGHT

A portion of the disclosure of this patent document contains material that is subject to copyright protection. The copyright owner has no objection to the facsimile reproduction by anyone of the software engine and its modules, as it appears in the Patent and Trademark Office Patent file or records, but otherwise reserves all copyright rights whatsoever.

FIELD OF THE INVENTION

Embodiments of the invention generally relate to systems, methods, and apparatus for solar-driven refining of biomass and other materials. More particularly, an aspect of an embodiment of the invention relates to quenching, gas cleanup, or ash removal in systems, methods, and apparatus for refining biomass and other materials.

BACKGROUND OF THE INVENTION

Biomass gasification is an endothermic process; energy must be put into the process to drive it forward. Typically, this is performed by partially oxidizing (burning) the biomass itself. Between 30% and 40% of the biomass must be consumed to drive the process, and at the temperatures which the process is generally limited to (for efficiency reasons), conversion is typically limited, giving still lower yields. In contrast, the proposed solar-driven biorefinery uses an external source of energy (solar) to provide the energy required for reaction, so none of the biomass need be consumed to achieve the conversion. This results in significantly higher yields of gallons of gasoline per biomass ton than previous technologies. As the energy source being used to drive the conversion is renewable and carbon free.

SUMMARY OF THE INVENTION

Some embodiments relate to systems, methods, and apparatus for solar driven refining of biomass and other materials with quenching, gas cleanup, and/or ash removal from the refined biomass or other materials.

An embodiment may include a solar-driven chemical plant and a solar thermal receiver aligned to absorb concentrated solar energy from one or more solar energy concentrating fields such as an array of heliostats, a solar concentrating dishes or any combination of these.

The solar driven chemical reactor may have multiple reactor tubes located inside the solar thermal receiver. In these reactor tubes particles of biomass can be gasified in the presence of, for example, a carrier gas in a gasification reaction. The gasification reaction may produce reaction products including hydrogen and carbon monoxide gas. Additionally, these gases may have an exit temperature from the tubes exceeding 1000 degrees C.

In an embodiment, a quench zone may be located immediately downstream of an exit of the chemical reactor. The quench zone can immediately quench via rapid cooling of at least the hydrogen and carbon monoxide reaction products. This cooling may occur within 0.1-10 seconds of the reaction products exiting the chemical reactor to achieve a temperature of 800 degrees C. or less. A temperature of 800 degrees C. or less is below a level to prevent metal dusting for some alloys, some coalescence of the ash product, and possibly prevent the hydrogen and carbon monoxide reaction products from the gasification reaction to revert back to other compounds.

Some embodiments include an on-site fuel synthesis reactor. The on-site fuel synthesis reactor can be geographically located on the same site as the chemical reactor and integrated to receive the hydrogen and carbon monoxide products, which have passed through the quench zone.

BRIEF DESCRIPTION OF THE DRAWINGS

The drawings refer to embodiments of the invention in which.

Figure 1:
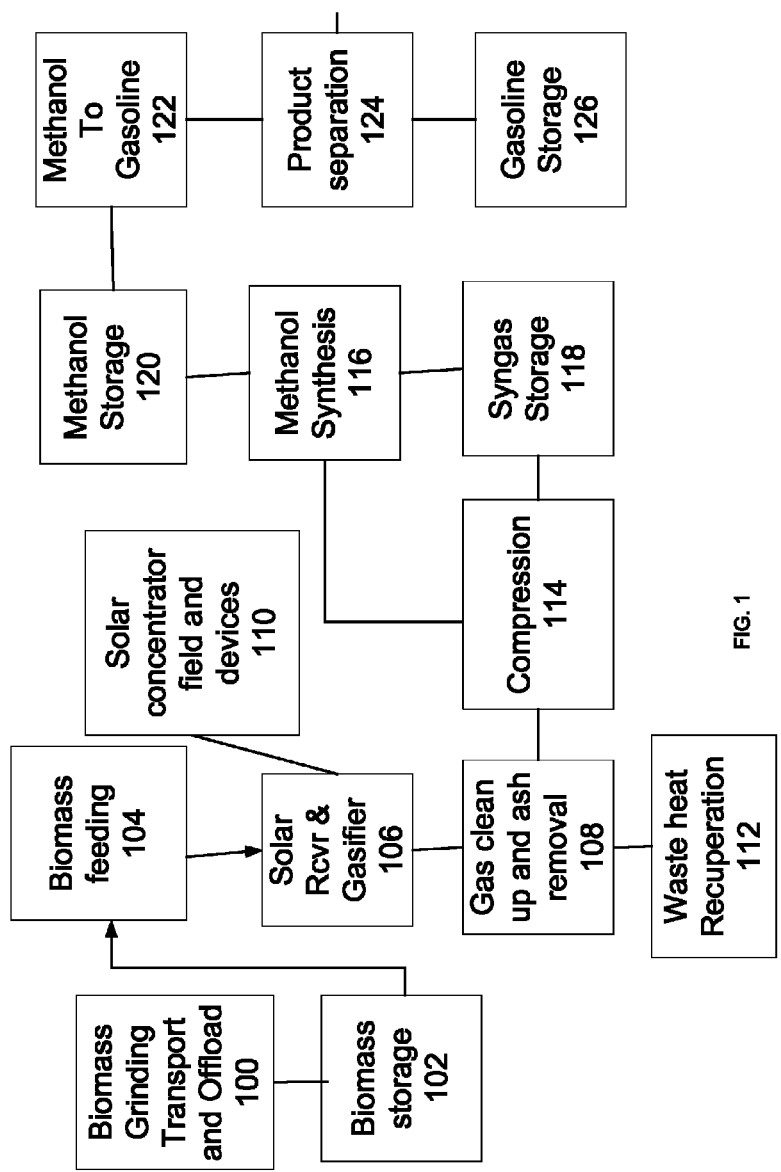
FIG. 1 illustrates a block diagram of an embodiment a solar-driven chemical plant such as a bio-refinery.

While the invention is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the invention.

DETAILED DISCUSSION

In the following description, numerous specific details are set forth, such as examples of specific data signals, named components, connections, number of reactor tubes, etc., in order to provide a thorough understanding of the present invention. It will be apparent, however, to one of ordinary skill in the art that the present invention may be practiced without these specific details. In other instances, well known components or methods have not been described in detail but rather in a block diagram in order to avoid unnecessarily obscuring the present invention. Further specific numeric references such as first reactor tube, may be made. However, the specific numeric reference should not be interpreted as a literal sequential order but rather interpreted that the first reactor tube is different than a second reactor tube. Thus, the specific details set forth are merely exemplary. The specific details may be varied from and still be contemplated to be within the spirit and scope of the present invention. The features discussed in an embodiment may be implemented in another embodiment. The term coupled is defined as meaning connected either directly to the component or indirectly to the component through another component.

In general, a solar-driven chemical plant can include a solar thermal receiver aligned to absorb concentrated solar energy from one or more solar energy concentrating fields such as an array of heliostats, a solar concentrating dishes or any combination of these.

A solar driven chemical reactor may have multiple reactor tubes located inside the solar thermal receiver. In the reactor tubes particles of biomass can be gasified in the presence of, for example, a carrier gas in a gasification reaction. The gasification reaction may produce reaction products including hydrogen and carbon monoxide gas. Additionally, these gases may have an exit temperature from the tubes exceeding 1000 degrees C.

The reactor tubes can serve the dual functions of segregating the biomass gasification reaction environment from the atmosphere of the solar receiver and transferring energy by solar radiation absorption and heat radiation, convection, and conduction to the reacting particles. This energy may drive the endothermic gasification reaction of the particles of biomass flowing through the reactor tubes.

In an embodiment, a quench zone may be located immediately downstream of an exit of the chemical reactor. The quench zone can immediately quench via rapid cooling of at least the hydrogen and carbon monoxide reaction products. This cooling may occur within 0.1-10 seconds of the reaction products exiting the chemical reactor to achieve a temperature of 800 degrees C. or less which prevents metal dusting on some alloys and preferably 400 degrees C. or less which prevents metal dusting on almost all alloys. A temperature of 800 degrees C. or less is below a level to reduce coalescence of ash remnants of the biomass particles.

FIG. 1 illustrates a block diagram of an example process flow in the solar driven syngas refinery. Some embodiments encompass a solar-driven-biomass gasification to liquid fuel/ electrical process. The process might also include generation, chemical processing, or bio-char, for solar generated syngas derivative product or other similar technical process. In a specific example implementation the process described is a solar-driven-biomass gasification to 'green' liquid fuel process. In an embodiment, this process includes one or more of the following process steps.

Biomass grinding or densification, transport, and then offload 100 may be part of the overall process. Bales of the biomass can be compressed and densified by a compactor to facilitate transport to on-site via the densification achieved by the compression and the bales are sized to dimensions that may, for example, fit within a standard box car size or shipping container size to fit within standard compactor size. The entrained-flow biomass feed system can be preceded by a grinding system equipped with mechanical cutting device and a particle classifier, such as a perforated screen or a cyclone, to control the size of the particles that are then fed into and gasified in the solar-driven chemical reactor.

Equipment generally used for grinding biomass includes impact mills (e.g. hammer mills), attrition mills, and kinetic disintegration mills-KDS (e.g. flail mills). A hammer mill system, KDS, or similar system can be used to grind the bales (loaded by conveyer) into particles, which are to be fed into the feed system for the solar thermal gasifier. The ground particles have an average screen size between 500 microns (um) and 1000 um in diameter, and are loaded into, a silo with a standard belt conveyer or with a positive or negative pressure pneumatic conveying system. The ground particles may also have an average screen size between 50 microns (um) and 1000 um, 50 microns (um) and 200 um, 50 microns (um) and 2000 um and various combinations.

The biomass may then be stored 102. As needed, the biomass will be fed 104 into an example solar-driven chemical reactor via a feed system. For example, after grinding and pulverizing the biomass to particles, a lock-hopper feed system feeds the particles of biomass into the solar-driven chemical reactor to be gasified. The feed system can supply the variety and types of biomass particles discussed above.

A solar receiver and gasifier 106 may be used to thermally decompose the biomass. An embodiment may include one or more apertures 1) open to the atmosphere of the Earth or 2) covered by one or more windows. In an embodiment, concentrated solar energy from the solar energy concentrating fields can pass through the apertures or windows into the solar thermal receiver. In this way, the solar energy may impinge on the multiple reactor tubes and cavity walls of the receiver. An example biomass gasifier design and operation can include a solar chemical reactor and solar receiver to generate components of syngas.

Note, a chemical reactor is the container in which a chemical reaction occurs. Also, the chemical reactor may be a single reactor tube, or a set of reactor tubes. Thus, the chemical reactor may be a single reactor with multiple reactor tubes or multiple reactors each being a single reactor tube, or some other similar combination. Further, multiple or different chemical reactions may take place in different reactor tubes of the solar-driven chemical reactor. For example, Steam Methane Reforming may occur in a first set of reactor tubes and biomass gasification may occur in another set of reactor tubes making up the chemical reactor, which is at least partially contained in the solar thermal receiver. Also, Steam Methane Reforming and biomass gasification may occur within the same reactor tube. In addition, the control system may control the chemical reactions occurring within the reactor tubes via a number of mechanisms as described herein. For example, the flow rate of the chemical reactants, such as biomass particles and carrier gas, into and through the reactor tubes is controlled, along with a concentration of each reactant flowing through the reactor tube. The control system may control each reactor tube individually, or in sets/groups of for example clusters of eighteen tubes, or all of the tubes in their entirety. The shape, orientation, and other features of the reactor tubes may vary. For example, the reactor tube may be circular, rectangular, or have another shape. Note, for contrast purposes, more than one chemical reactor may be located on a common tower. For example, a first chemical reactor, a second chemical reactor, and a third chemical reactor may be contained at least partially within its own associated solar thermal receiver. The first, second, and third chemical reactors located on the same tower may not share a common control system or a common solar thermal receiver, and thus, are truly each distinct chemical reactors. However, they all may be fed from some common feed vessels/lock hoppers and/or may share downstream quenching and gas clean up system components. Note, in large production facility with multiple towers and corresponding receivers and solar driven reactors, each system may have receiver specific control systems but may also share a control system. There may be a field wide control system on top of tower level systems on top of receiver specific systems.

Various heliostat field designs and operations to drive the biomass gasifier might be used. Some example designs may include a solar concentrator, secondary concentrator, focused mirror array, etc. to drive biomass gasifier 110.

Quenching, gas clean up, and ash removal from biomass gasifier 108 may be provided for. Quenching via rapid cooling of at least the hydrogen and carbon monoxide reaction products may occur within 0.1-10 seconds of exiting the chemical reactor to achieve a temperature of 800 degrees C. or less immediately downstream of an exit of the chemical reactor. The rapid cooling to a temperature of 800 degrees C. or less is below a level to prevent the hydrogen and carbon monoxide reaction products from the gasification reaction to revert back to other compounds if not cooled by the immediate quench as well as the quench partially occurs to prevent coalescence of ash remnants of the biomass particles, such as slagging and scaling. In an embodiment, the quench zone cools the temperature to 400 degrees C. or less within the 0.1-10 seconds immediately downstream of the exit of the chemical reactor and this prevents metal dusting corrosive degradation of metals and alloys in the strongly carburizing effluent atmosphere as well as minimizes an amount of time for a water gas shift reaction to occur and generate CO2 as a byproduct. In an embodiment, this rapid cooling occurs with 2-15 seconds.

Some gasses may be a waste product, while other gasses can be compressed 114 prior to storage 118 or e.g., methanol synthesis 116. Methanol may then be stored 120 for later methanol to gasoline conversion 122.

In various embodiments, synthesis gas may be feed to another technical application. Examples include a syngas to other chemical conversion process. The other chemical of chemicals produced can include liquefied fuels such as transportation liquefied fuels. Some transportation liquefied fuels include jet fuel, DME, gasoline, diesel, and mixed alcohol, bio-char with a high sequestered amount of carbon; chemical production, electricity generation, synthetic natural gas production, heating oil generation, and other similar syngas based technical applications. In an example hydrocarbon based fuel, e.g., methanol, 116 may be formed from syngas. The methanol may be further converted to gasoline or other fuels 122 and various products may be separated out from the gasoline 124 or syngas. These products, e.g., gasoline, may then be stored for later use as an energy source.

In one example, the solar-driven biorefinery may process multiple types of biomass and be located in or near a region with abundant biomass sources in order to produce "green" gasoline. Solar thermal energy may be used to drive gasification of biomass, upgrading the heating value of the feedstock with a renewable energy source, while allowing operation at temperatures where tar formation is negligible. The biorefinery may be built in an area having easy access to the Sun as well as to a variety of biomass feedstock.

In an embodiment, an on-site fuel synthesis reactor has an input to receive the hydrogen and carbon monoxide products from the gasification reaction and configured to use the hydrogen and carbon monoxide products in a hydrocarbon fuel synthesis process to create a liquid hydrocarbon fuel. For example, synthesis gas may be processed using many different technical applications as discussed above. For example the solar generated syngas can be used with proven catalytic processes into intermediate methanol, and then subsequently into gasoline via the MTG process. Alternatively, the on-site fuel synthesis reactor may be a synthesis gas to methanol reactor that produces liquid methanol. In an embodiment, the biorefinery will be the first solar unit integrated with a downstream liquid transportation fuels plant. Thus, the fuel synthesis reactor may be geographically located on the same site as the chemical reactor and integrated into the process to utilize the hydrogen and carbon monoxide products from the gasification reaction. The on-site fuel synthesis reactor may be connected to the gas clean up section be less than 10 miles of piping and be wired to bi-directionally send feedback information between the on-site fuel synthesis control system and the control system for the solar driven chemical reactor. Synthesis gas will be processed using proven catalytic processes into intermediate methanol, and then subsequently into gasoline via the MTG process.

In some embodiments, the entrained-flow biomass feed system includes a computerized control system configured to balance the amount of biomass particles flowing in each of the reactor tubes to an amount of solar energy available. For example, the control system may send a signal to control flow in the individual reactor tubes by controlling mechanisms such as a rotational rate of a screw of a lock hopper feeding the biomass, a rotational rate of airlock type metering device, changing an amount of reactor tubes participating in the gasification reaction, an amount of compression of a flexible pipe section applied to each individual feed line that the biomass particles are flowing through, etc. As noted, the biomass feedstock resources can include energy crops such as miscanthus and switchgrass, which are high-impact and high-yield energy crops. A biomass with low lignin content is easier to gasify and process in the solar gasifier.

Figure 2:
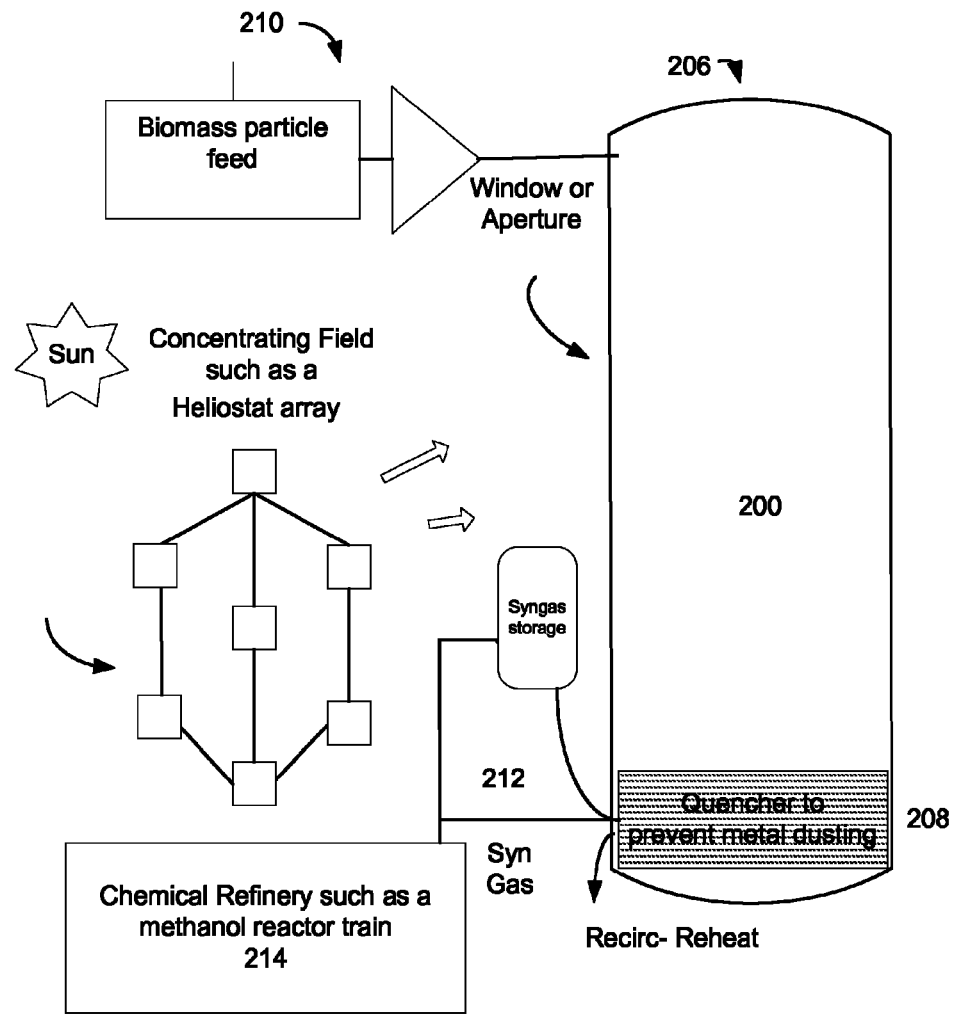
FIG. 2 illustrates a diagram of an embodiment of a solar-driven chemical plant.

FIG. 2 illustrates a diagram of a solar-driven chemical plant 200 in accordance with the systems and methods described herein. In such a system solar power 202 may be provided through a window or aperture 204 to a solar heated reactor chamber 206. A quencher 208 may be used to prevent back reaction. As illustrated, biomass particles flow into the system at 210 and syngas flows out 212. Additionally, a heat exchange may occur between the biomass particles and the syngas.

A solar-driven chemical plant 200 may include a solar thermal receiver aligned to absorb concentrated solar energy from one or more solar energy concentrating fields including 1) an array of heliostats, 2) solar concentrating dishes, and 3) any combination of the two.

An embodiment can include a solar driven chemical reactor that has multiple reactor tubes located inside the solar thermal receiver. In the multiple reactor tubes, particles of biomass may be gasified in the presence of a carrier gas in a gasification reaction. The gasification can produce reaction products that include hydrogen and carbon monoxide gas having an exit temperature from the tubes exceeding 1000 degrees C.

An embodiment may include one of 1) one or more apertures 1) open to an atmosphere of the Earth or 2) covered by one or more windows. The apertures or windows may be configured to pass the concentrated solar energy from the solar energy concentrating fields into the solar thermal receiver. The energy can impinge on the multiple reactor tubes and cavity walls of the receiver. Additionally, the reactor tubes serve the dual functions of 1) segregating the biomass gasification reaction environment from the atmosphere of the solar thermal receiver and 2) transferring energy by solar radiation absorption and heat radiation, convection, and conduction to the reacting particles. This energy may drive the endothermic gasification reaction of the particles of biomass flowing through the reactor tubes.

As discussed, the quench unit rapidly cools the reacted biomass products from the gasification reaction as well as the resultant ash and un-reacted biomass. The quench unit may make use of the heat energy removed during the rapid cooling. For example, some embodiments may include a torrefaction unit. This torrefaction unit may be on the same site as the solar-driven chemical plant 200. Biomass may be processed to partial pyrolysis with recouped waste heat (100-300° C.) from the quench unit. Using recouped waste heat may make the biomass 1) brittle and easier for grinding, 2) dryer, less sticky, and easier to feed in conveying system, 3) subject to less spoilage issues in storage as a torrefied biomass, as well as 4) produce off gases from the torrefaction process. The off gases might be used for the entrainment gas, steam generation, or electrical generation.

The grinding system receives the partially torrified biomass and has a mechanical cutting device and a series perforated filters used to grind the partially pyrolyzed biomass from the torrefaction unit to control the particle size of the biomass to be between 50 and 2000 um with a preferred range of 500 um and 1000 um. The torrefaction unit reduces the energy required to grind the biomass to the controlled particle size.

Figure 3:
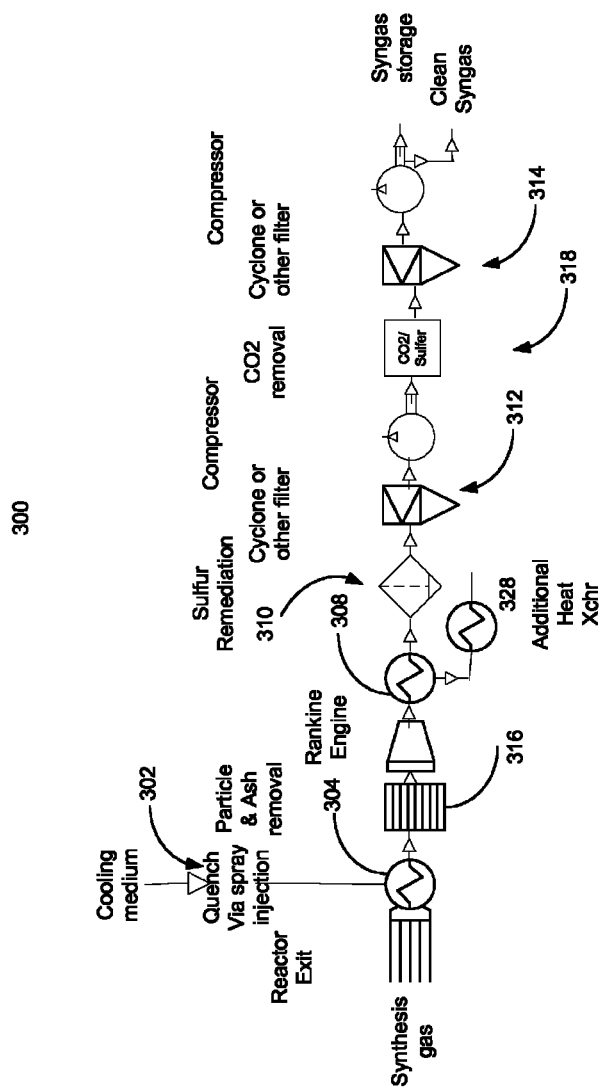
FIG. 3 illustrates a diagram of an embodiment of a quenching, gas clean up, and ash removal system.

FIG. 3 illustrates a diagram of an embodiment of a quenching via an injection of cooling medium into the reaction products, gas clean up, and ash removal system. Direct quenching methods of cooling the hot reaction products via for example direct spraying of cooling mediums into the stream carrying the hot reaction products causing the cooling of the hot reaction products are discussed in FIG. 3. Other example methods such as annular quenching methods of cooling the pipe carrying the hot reaction product from the solar driven reactor via heat transfer through the pipe are discussed, for example in FIG. 4. Features described in one embodiment may be used in another embodiment.

The solar-driven chemical plant may directly cool the reaction products from the effluent stream out of the solar driven reactor. One or more spray nozzles in the quench zone spray a liquid cooling fluid directly into the reaction product stream from the solar driven chemical reactor. The direct spraying of a liquid cooling fluid into the stream carrying the hot reaction products causes the liquid cooling fluid to vaporize into a superheated gas. The liquid cooling fluid, such as water, becomes a superheated vapor, such as superheated steam, extracting the energy from the hot reaction products.

A control system controls one or more of the following plant parameters to ensure the temperature is at or below 400 C when leaving the quench zone, where the control system 1) changes a flow rate of a cooling medium being sprayed into the hot reaction products, 2) provides feedback to change the flow rate of biomass into the solar driven chemical reactor, or 3) directs the concentrating field to change an amount of concentrated solar energy being directed at the aperture of solar thermal receiver.

Thus, the quench zone may form near an exit of a gasification reaction zone in the reactor tubes of the chemical reactor so as to not crack or not thermally affect the reactor tubes. Two or more of the multiple reactor tubes may form into a group at the exit and that group combines their reaction products and un-reacted particles from the biomass gasification into a larger tube per group that forms a portion of the quench zone or all of the tubes may supply the reaction products into a common manifold that forms a portion of the quench zone.

The one or more sprayers, such as valves and nozzles, located inside the quench zone inject the cooling fluid directly into the reaction product syngas stream to make the temperature transition from the at least 1000 degree C. to less than 400 degrees C. within the 0.1-10 seconds to further prevent metal dusting corrosion of the pipe walls and minimizes an amount of time for a water gas shift reaction to occur and generate CO2 as a byproduct.

A particle filter removal component downstream of the quench zone removes ash and other particles from the superheated gas and hot reaction products supplied from the quench zone. The particle filter may also remove some of the moisture content in the superheated gas. The particle filter may also remove some corrosive or otherwise undesired chemicals that could be damaging to the Rankine cycle engine. The hot reaction products and superheated gas can used as a medium to drive a Rankine cycle engine, such as a turbine, to draw the energy from the super heated vapor form of the cooling medium and hot reaction products. The Rankine cycle engine has an input to receive the hot reaction products and superheated gas. The super heated vapor form of the cooling medium and the hot reaction products after transferring their energy through the Rankine cycle change states to a saturated vapor heavy in moisture content. The Rankine cycle engine may be inline to receive the superheated gas vapor or connected to a heat exchanger, which extracts the majority of heat energy out of the super heated gas vapor.

Thus, the super heated vapor form of the cooling medium and hot reaction products after transferring their energy change states to a saturated vapor heavy in liquid. The saturated vapor heavy flow through one or more knock out drums to dry the vapor, which then can run an organic turbine in another Rankine cycle or transfer its energy via a steam condensing heat exchanger. Thus, the knockout drums located downstream of the Rankine engine remove entrained water or other moisture from the syngas stream supplied from the quench zone.

A CO2 removal unit sits behind the knockout drum and removes CO2 from the syngas stream supplied from the quench zone. The CO2 content of the syngas stream is reduced by the CO2 removal unit to CO2 to less than 15% and a preferred range of 2-7% of the syngas stream. Also, a sulfur remediation unit is located downstream of the quench zone to reduce an amount of hydrogen sulfide present in a syngas stream containing at least the carbon monoxide and hydrogen molecules from the gasification reaction down to a level equal to or below 100 ppb and preferably 50 ppb of sulfur in the syngas stream. Note, an amine unit would remove both sulfur and CO2. However, if the sulfur levels are below the threshold due to sulfur removal via metal oxide particles being present in the reactor chemical reactor and/or quenching process, then an amine unit to remove both CO2 and Sulfur may be replaced with just a CO2 filter.

In an embodiment, the sulfur remediation component reduces an amount of sulfur present in a syngas stream down to a level equal to or below 100 ppm.

The sulfur remediation component may be located after the rapid quench zone and the particle filter removal component but before the CO2 removal unit.

The syngas coming to the compressors for storage or the methanol plant supply is high quality syngas. The greater than 1000 degree C. temperature of the reaction products from the chemical reactor is a high enough temperature for the greater than 90 percent conversion of the biomass particles to product gases and eliminates tar products to less than 200 mg/m^3 and preferably less than 50 mg/m^3. Also this renewable syngas is an unusually clean because the sulfur level is controlled, CO2 removal occurs in the CO2 removal unit, water and other moisture removal occurs in the knockout drums, and particle filter removal occurs in the particle filter removal component.

In an embodiment, the syngas must have total tar concentrations below 200 mg Nm-3, catalyst poison concentrations below 100 ppb for H2S, HC1, and NH3, and have a H2:CO ratio within the example range 2.3 to 2.7. These compositional concentration measurements will be taken periodically during gasifier operation through FTIR spectroscopy and gas chromatography periodically and measured with other detectors on a steady state basis. These parameters may be fed to the control system to ensure that synthesis gas composition does not vary (+/−10%) from the desired composition, as well as to verify that catalyst poison concentrations are not above deactivation thresholds for the methanol synthesis catalyst.

Ash measurements will be made one or more times daily and mass balances will be performed to ensure that overall biomass conversion remains above threshold targets and that alkali deposits are not being formed on the inside of the reactor.

The injection of the cooling fluid in the quench zone may be controlled to also alter the chemical composition of the gas stream necessary to achieve the proper H2 to CO ratio of syngas composition necessary for fuel synthesis, such as a 2:1 to 2.8:1 H2 to CO ratio. The controlled reactions may include one or more of the following example reactions.

1) Water injects and mixes with the reaction product syngas stream in order for an exothermic water gas-shift reaction to occur (CO+H2O→CO2+H2+energy) for increasing hydrogen and decreasing carbon monoxide.

2) Carbon dioxide is supplied with the natural gas entrainment gas, and/or generated in the biomass gasification reaction and becomes part of the reaction product syngas stream in order for decreasing hydrogen and increasing carbon monoxide in an endothermic reverse water-gas shift reaction to occur (CO2+H2+energy→CO+H2O).

3) Methane, and low temperature water injects and mixes with the reaction product syngas stream in the presence of a catalyst to drive the endothermic steam reformation of methane to occur (CH4+H2O+energy→3H2+CO) for increasing an amount of hydrogen relative to the carbon monoxide.

Figure 4:
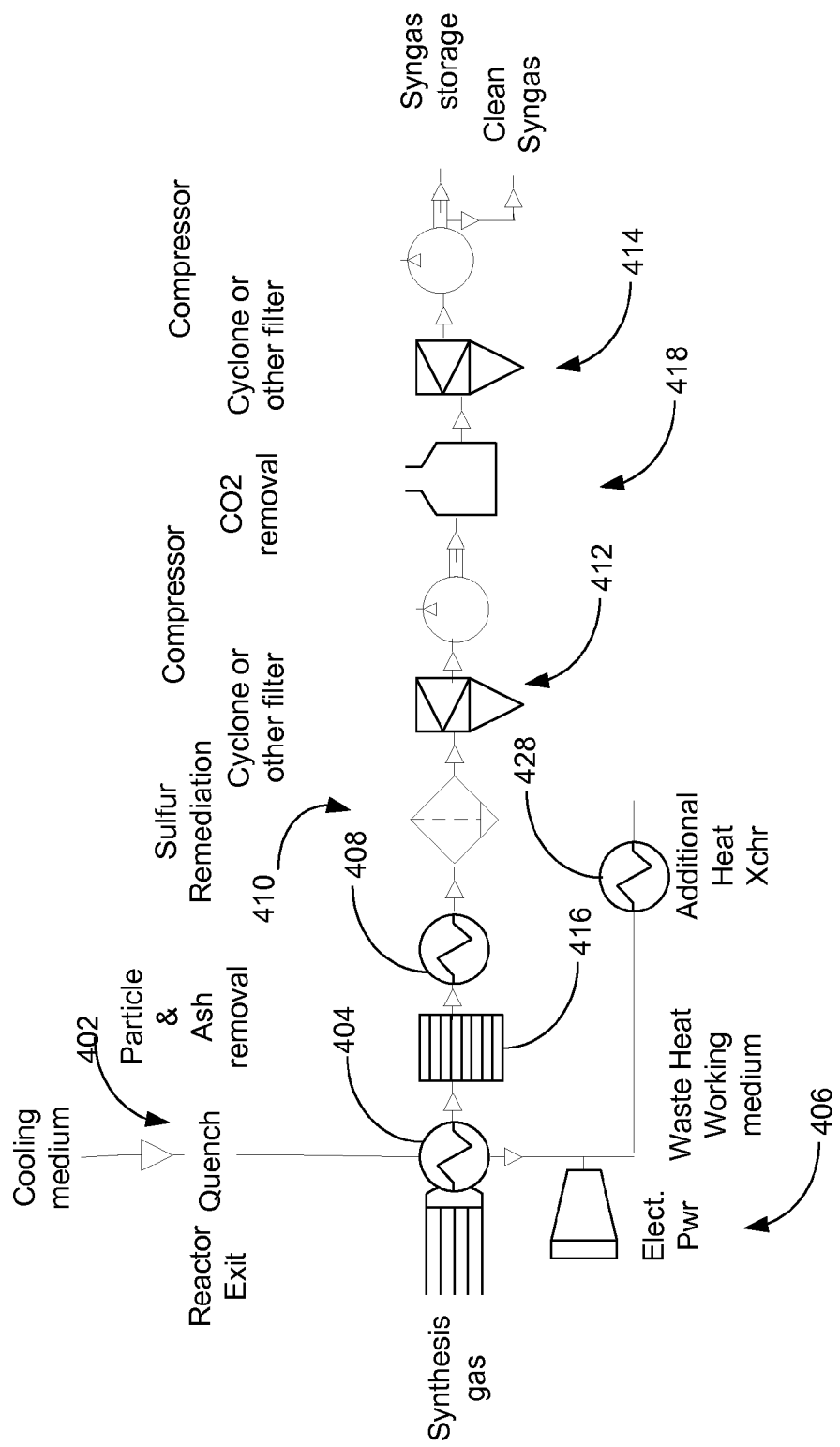
FIG. 4 illustrates a diagram of another embodiment of a quenching, gas clean up, and ash removal system.

FIG. 4 illustrates a diagram of an embodiment of a quenching with an annular based quench zone, gas clean up, and ash removal system 300b. In an embodiment, a quench zone 302b located immediately downstream of an exit of the chemical reactor may be used to immediately, quench via rapid cooling, at least the hydrogen and carbon monoxide reaction products.

In an embodiment, a solar-driven bio-refinery may include an exit of a gasification reaction zone in the reactor tubes of the chemical reactor. At the exit, the reaction products and un-reacted particles from the biomass gasification in the multiple tubes may be joined into several large tubes that form a portion of the quench zone 302b. In an alternative embodiment, a quench zone 302b design may include dumping the reactor products from some or all of the reactor tubes into a manifold, and then into one or more syngas tubes containing the reaction product syngas stream of reaction products and un-reacted particles. Each tube may also be individually quenched.

In an embodiment, a quench zone 302b immediately downstream of an exit of the chemical reactor may be used to immediately quench via rapid cooling of at least the hydrogen and carbon monoxide reaction products. For example, the quench zone may be used to immediately and rapidly cool at least the hydrogen and carbon monoxide reaction products within 0.1-10 seconds of exiting the reactor to a temperature of 800 degrees C. or less and preferably 400 degrees or less. In an embodiment, quenching the hydrogen and carbon monoxide reaction products within 0.1-10 seconds of exiting the reactor to 500 degrees C. or less prevents metal dusting from occurring in most alloys. The quench zone generally rapidly cools the reacted biomass products from the gasification reaction as well as the resultant ash and un-reacted biomass. In some embodiments, the cooling might occur within 0.1-10 seconds of exiting the chemical reactor and cooling to a temperature of 400 degrees C. or less. Generally, 800 degrees C. is below a level to prevent the hydrogen and carbon monoxide reaction products from gasification reaction to revert back to other larger hydrocarbon compounds if not cooled by the immediate quench. Additionally, the quench may prevent coalescence of ash remnants of the biomass particles. The cooling to less than 400 degrees C. should prevent metal dusting.

An immediate quench and, in some embodiments, a second partial quench may prevent coalescence of ash remnants of the biomass particles. Rapid quenching may occurs in the quench zone 302b to get temperature from, e.g., 1050 degrees C.-1100 degrees C. down to at least 400 degrees C. This quenching may prevent metal dusting, prevent coalescence of ash remnants, and possibly minimize Boudouard carbon formation. Some ways used to achieve this rapid quenching of the reactor exit products that occurs in the quench zone, individually or in combination, include using a heat exchanger and/or introduced cooling medium.

In an embodiment, the solar-driven chemical plant may include a heat exchanger 304b forming part of the quench zone 302b. The heat exchanger 304b in the quench zone 302b may be used to quench and cool the reaction products exiting the reactor tubes. The quench zone 302b may use a cooling medium fed through a heat exchanger 304b to quench and cool the reactor products exiting the reactor. For example, the reactor tubes, which may come out of a reaction zone of the chemical reactor and make the temperature transitions, can be jacketed to form the heat exchanger 304b.

A cooling medium or cooling fluid such as water/steam may be passed on an inside through heat exchanging tubes in the annular region of the quench zone 302b to cool the reaction product syngas stream on the outside of the heat exchanging tubes. Additionally, one or more supply pipes may introduce a cooling medium with the reaction products. The heat exchanger 304b may introduced a cooled medium in one or more of a tail gas of N2, CO2, low temperature syngas recycled from a storage tank, or other similar tail gas.

In an embodiment, the cooling medium can be passed through the heat exchanging tubes in the annular region of the quench zone to cool the product syngas stream and recuperate waste heat from the product syngas stream. The cooling medium can carry waste heat away from the quenching exits the heat exchanger 304b. In an embodiment, the heated cooling medium may use recouped waste heat to preheat feed gas or particles prior to entry into the reactor via a counter flow heat exchange method or similar method.

For example, a heat exchanger, such as counter flow, cross flow, etc., may be used to receive the cooling medium. The carrier gas can be heated by the cooling medium carrying the waste heat of the reaction products in the heat exchanger. The heat exchanger may also be part of or merely receive a pipe from the cooling jackets around the transition metals.

In an embodiment, waste heat carried away by this cooling medium might be used to pre-heated the biomass particles, e.g., up to a maximum temperature of 300 degrees C. prior to entry into the chemical reactor by the carrier gas. For example, the biomass particles may be pre-heated prior to entry into the chemical reactor by, e.g., CO2 gas or steam, or other carrier gas. The counter flow heat exchanger could heat the entrainment gas carrying the biomass particles up to 300 degrees C. The waste heat might also heat the carrier gas up to, e.g., a maximum temperature of 300 degrees C. For example, the carrier gas can be heated by waste heat from the products of the gasification reaction coming out of the chemical reactor by the counter flow heat exchanger using the waste heat as its heat source.

In an embodiment, heat recovery in the exit stream of the gasifier may be used. This might be done using a shell and tube style heat exchanger. In such a system, the process gas may pass through the tubes and the recuperating gas or liquid may pass through the shell side. The recuperant on the shell side could be boiling water, a molten salt, or supercritical CO2, for example.

In an embodiment, the solar-driven bio-refinery may pneumatically feed particles of biomass from an entrained-flow biomass feed system. This may be done via a carrier gas driven into to the solar driven chemical reactor. In an embodiment, a solar-driven chemical plant can include an entrained-flow biomass feed system to feed the particles of biomass in a CO2 gas or steam carrier gas to the reactor tubes of the solar driven chemical reactor.

In some embodiments, a solar-driven chemical plant may include a Brayton engine to generate to electricity and act as a heat sink for the quench zone. In such a system, the quench zone $302b$ can have a cooling medium fed through a heat exchanger $304b$ to quench and cool the reaction products exiting the reactor. The heated cooling medium leaving the heat exchanger $304b$ might use recouped waste heat from the quench process to drive the Brayton engine to generate to the electricity $306b$. One example embodiment may use quenching and cooling reactor products including the syngas gas out of the reactor with a Brayton engine run at least 900 degrees C. to generate to electricity. Additional heat exchangers $308b$ might also be used to provide additional cooling or drive the Brayton engine to generate to the electricity. Recuperated heat in a Brayton cycle engine may generate electrical power. For example, such an engine could run on air, other gases, or supercritical CO2, heated using waste heat, for example.

Depending on the embodiments, different quench zones described above for the temperature transition from operating temperature to less than 800 degrees C., the tubes carrying the gases and particles from the reactor may be made of a single material or compound or have multiple sections of different materials or compounds. In the case of multiple sections, the tubes containing the un-reacted and reaction products from the gasification reaction have each section composed of a different material able to withstand the quenching conditions occurring in that section. Generally, the material making up a first section of the tube is different than a material making up a second section of the tube.

Upon leaving the reactor, the synthesis gas product may be cooled and the material of the tubes carrying the synthesis gas product may be formed in sections. The reactor tubes can be made of graphite, for example, in the quench zone $302b$ to allow for an initial transition to high temperature alloy such as inconnel or a similar alloy. For example, the reactor tubes may be made of high temperature material that can contain the syngas and other reaction products at high temperature.

Once the temperature of the syngas and other reaction products is low enough, the tubes carrying the syngas can make a final transition to a low temperature material. For example, the pipe or tube carrying the syngas may transition to a low temperature metal such as stainless thru to carbon steel, etc. The tubes can also be jacketed and cooling water, steam, etc. may be passed through the annular region to cool the product stream and recuperate heat.

In an embodiment, the cooling jacket covers at least a portion of the tubes making the temperature transition, which allows the use of lower temperature tolerant transition materials to carry the syngas and reaction products downstream of the chemical reactor in the quench zone $302b$ and aids in the quench.

In an embodiment, a solar-driven chemical plant can include one or more cooling jackets. For example, cooling jackets may cover tubes made of transition metals that carry syngas. This may aid in the quench and allow the use of lower temperature tolerant materials to carry the syngas downstream of the reactor including in the quench zone.

In an embodiment, the reactor tubes that come out of the gasification reaction zone may be jacketed and make a temperature transition from the at least 1000 degree C. to less than 400 degrees C. A cooling fluid, such as water/steam, may be passed through the jacket to cool the tubes containing the reaction product syngas stream making the temperature transition.

One or more injection pipes in the quench zone $302b$ can be located at or near the exit of the gasification reaction zone of the reactor tubes. A cooling compound consisting of at least one of 1) low temperature water (H2O), 2) methane (CH4) with low temperature water and oxygen, 3) low temperature methanol (CH3OH), and 4) various combinations can be injected into the pipes, e.g., syngas tubes and/or manifold. This can simultaneously 1) rapidly cool the reaction product syngas stream from the at least 1000 degree C. to less than 800 degrees C. and 2) provide chemical compounds necessary to achieve a proper H2 to CO ratio of syngas necessary for fuel synthesis. Additionally, the energy to cause the endothermic reactions may be contained in the reactor products, e.g., the energy may come from heat contained in the reaction product syngas stream.

In some embodiments, the chemical compounds necessary to achieve the proper H2 to CO ratio of syngas composition necessary for fuel synthesis, such as a 2:1 to 2.7:1 H2 to CO ratio, include: 1) injecting water, and/or hydrogen, and/or carbon monoxide, and/or carbon dioxide in various combinations in the reaction product syngas stream in order for at least one of the following reactions to occur and shift the H2 to CO ratio. A) An exothermic water gas-shift reaction to occur (CO+H2O→CO2+H2+energy) for increasing hydrogen and decreasing carbon monoxide, and B) an endothermic reverse water-gas shift reaction to occur (CO2+H2+energy→CO+H2O) for increasing carbon monoxide and decreasing hydrogen. 2) Methane, and low temperature water can be injected and mixed with the reaction product syngas stream to drive the endothermic steam reformation of methane to occur (CH4+H2O+energy→3H2+CO) for increasing an amount of hydrogen relative to the carbon monoxide. With either of the above H2 to CO ratio shifting reactions, later injecting low temperature methanol to further cool the syngas and other reaction products traveling in the quench zone. The injected cooling compound injected may be in a liquid state to remove more energy from the syngas stream of reaction products due to the heat of vaporization affect on the injected cooling compound.

The exothermic water-gas shift reaction discussed above may also be referred to as a Water Gas Shift/Dussan Reaction. It is a chemical reaction in which carbon monoxide reacts with water vapor to form carbon dioxide and hydrogen: CO+H2O→CO2+H2. The endothermic RWGS may produce the resultant H2+CO molecules for the synthesis gas. (CO2+H2→CO+H2O) In another variant of the reverse water gas shift reaction, the formula may be represented as (2 CO2+3H2+energy→2 CO+3H2O). The RWGS may occur in the presence of a catalyst such as a Nickel alloy, Ni/Al2O3, etc. The exit syngas from with the RWGS or WGS, may then be immediately cooled/quenched in the quench zone to stabilize or otherwise capture the 2:1 ratio of H2 to CO. The endothermic steam reformation of methane CH4+H2O→3H2+CO.

In an embodiment, after the reactor, the quench zone $302b$ injects via spraying liquid water to obtain water gas shift stages (steam reformation) to increase CO production and for quenching between the temperature ranges of 450 C-750 C. The process may cause both cooling and create the syngas in the proper H2 to CO ratio at the same time. In addition, the process may also feed biomass particles with steam and perform a water gas shift during the gasification reaction to obtain a 2:1 to 2.7:1 H2 to CO ratio.

For example, water can be supplied and mixed with the hydrogen, carbon monoxide, and carbon dioxide in the reactor products in order for a water gas-shift reaction to occur. The water gas-shift reaction may be either the endothermic reverse water-gas shift reaction for increasing carbon monoxide and decreasing hydrogen or the exothermic water-gas shift reaction for increasing hydrogen and decreasing carbon monoxide. After the reactor, the quench zone injects via spraying water to obtain water gas shift stages (steam reformation) to increase CO production and for quenching between the temperature ranges of 450 C-750 C. In this way, the process may cool and put the syngas in the proper H2 to CO ratio at the same time. In addition, the process may also feed biomass particles with steam and perform a water gas shift during the gasification reaction to obtain a 2:1 H2 to CO ratio feed biomass particles with methane and perform steam reformation to obtain the 2:1 H2 to CO ratio, or both.

In an embodiment, a solar-driven chemical plant may include a syngas stream including carbon monoxide and hydrogen molecules that come out from the quench zone 302b. A knockout drum may be located downstream of the quench zone and may be used to remove entrained liquid droplets, such as water droplets, from the syngas stream supplied from the quench zone 302b.

In an embodiment, a series of sintered porous stainless steel metal filters 312b, 314b to remove particulates from the syngas stream exiting the quench zone may be used. The particulates can be sent to an ash holding vessel. In such a vessel the particulates can be staged for removal to be used as a soil additive, as the particulates contain only biologically derived materials and gypsum from a sulfur removal sorbent.

In an embodiment, a solar-driven chemical plant includes a sulfur remediation unit 310b downstream of the quench zone 302b. The sulfur remediation unit 310b can reduce an amount of sulfur present in a syngas stream. Such a remediation unit 310b may reduce an amount of sulfur in a syngas stream, containing at least the carbon monoxide and hydrogen molecules, from the gasification reaction down to equal to or below 100 ppb and preferably 50 ppb of sulfur in the syngas stream. The sulfur removal sorbent 310b may be present in the biomass gasification process or initially introduced in the quench zone 302b, to reduce an amount of sulfur present in a syngas stream exiting the quench zone 302b. For example, In an embodiment, the solar-driven chemical plant may include one or more supply lines to co-feed sorbent metal oxide particles, such as sorbent zinc oxide particles, with biomass particles that pass through the reactor tubes, such as the reaction products from the chemical reactor into the quench zone. This can occur during the biomass gasification reaction to remove the sulfur in the gaseous products from the reaction products coming out with the effluent stream.

In an embodiment, a multiple stage cyclone filters can be located before the sulfur remediation unit to allow un-reacted biomass recycling with cyclone separation. A first heavy cyclone stage can be constructed to remove heavy particles and a second lighter cyclone stage can be constructed to remove lighter particles consisting mainly of un-reacted biomass. The substantially particle-free syngas then passes into the sulfur remediation unit.

Particle-free or nearly particle-free gas may then pass into the sulfur remediation unit of ZnO polishing beds. In an embodiment, the beds contain, for example, 187 pounds of ZnO. Additionally, they may be in place to take the concentration of H2S from 10 ppm down to levels below 50 parts per billion. Replacement of the sorbent may need to take place periodically, such as every 100 days of full capacity operation.

The co-fed metal oxide particles, e.g., zinc oxide particles, may be selected to be most effective in sulfur removal in the 700-900 degree C. range and remove sulfur from the reaction products entering the quench zone 302b to a syngas stream exiting the quench zone 302b to equal to or below 100 ppb and preferably 50 ppb of sulfur in gaseous components of the syngas stream. For example, sorbent metal oxide particles removing sulfur during the biomass gasification reaction may include one or more from the group consisting of lime (CaO), zinc oxide (ZnO), and magnesium oxide (Mn3O4). Co-fed ZNO may be most effective in sulfur removal in the 700-900 degrees C. range and thus may be supplied and introduced as particles into the syngas in the quench zone.

In an embodiment, lime (CaO) can be preferred because the end product is gypsum, which may be used as fertilizer. If the co-fed metal oxide sulfur removing particles and the steam reformation reaction create under 15% and a preferred range of 2-7% CO2 in the syngas, then amine beds might not be used. Additionally, the syngas may have different ranges of entrained gases depending upon upstream reactions performed.

Some embodiments may use amine for sulfur removal if the metal oxide is not effective enough. The process can co-feed metal oxide particles with the biomass particles that pass through the reactor. Sulfur remediation occurs via a sorbent metal oxide, such as CaO, ZnO, magnesium oxide Mn3O4, etc., during the syngas generation reaction to remove the sulfur from the syngas.

A further syngas sulfur remediation component can be located after the rapid quench zone and particle filter removal components before any amine treatment plant. The particle-free gas then passes into the sulfur removal polishing beds. These sulfur removal beds contain ZnO, fly ash, CaSO4 sorbents, or similar compounds and they are in place to take the concentration of H2S from 10 ppm down to levels below 50 ppb. The zinc oxide adsorbent forms zinc sulfide, effectively trapping the sulfur: $ZnO+H2S \rightarrow ZnS+H2O$. The placement of the ZnO polishing beds can be right after particulate removal and before any amine treatment plant.

A particle filter removal component 316b may be located downstream of the quench zone 302b where ash and other particles are removed from the syngas stream supplied from the quench zone. Additionally, a CO2 removal unit 318b, such as an amine acid gas removal unit, may sit behind the knock-out drum. Such a CO2 removal unit 318b removes CO2 from the syngas stream supplied from the quench zone. For example, CO2 content of the syngas stream may be reduced by the CO2 removal unit to CO2 being less than 15% and a preferred range of 2-7% of the syngas stream.

In an embodiment, a syngas sulfur remediation component, including a zinc oxide adsorbent bed, may be used. Such a syngas sulfur remediation component may remove sulfur gas and other sulfur compounds from the syngas stream supplied from the quench zone. The sulfur remediation component may be located after the rapid quench zone 302b and the particle filter removal component 316b but before the CO2 removal unit 318b. In such a location the reaction products temperature may be less than 400 degree C.

In an embodiment, after leaving the polishing beds, the syngas passes through heat exchangers, additional water, or both. The syngas may also pass through light particle knock-out drums. This may cool and clean the syngas gas stream to the appropriate temperature for the CO2 removal unit. One example CO2 removal unit is an amine plant. The synthesis gas can subsequently enter a knockout drum, where entrained water can be removed. A CO2 removal unit such as an amine acid gas removal unit can sit behind the knockout drum and removes CO2, which is vented to the atmosphere. The CO2 content of the product synthesis gas can be, for example, dropped from 17% to 5%, and the product syngas may pass into a second knockout drum, which further dries the gas stream. In some embodiments, amine treatment may or may not occur to remove CO2 from entering the Syngas to methane process.

In an embodiment, the amine unit removes CO2 to required levels for synthesis of methanol. The syngas output from the quench zone can be rich in carbon dioxide because of the reverse water gas shift, the water gas shift reaction in the quench zone, or both. This can give the right H2 to CO ratio for synthesis and that occurs concurrently within the cooling zone for the solar reactor. For example, the syngas mole fraction is around 17% of the exit stream composition. The removal of this carbon dioxide for the syngas coming out of the reactor has a number of solutions beyond amine unit separation of CO2.

In an embodiment, exit particles from the reactor such as ash, un-reacted metal, biomass particles, or a combination of these, may be removed from the process. For example, one embodiment includes a separator. The separator can be configured to separate particles and ash remnants from the gas products of the reactor products into an ash and particle storage mechanism. This removal may occur at high temperatures during a quench. For example, these particles may exit the solar driven chemical reactor at the greater than 1000 degrees C. Alternatively, the removal may occur later at lower temperatures right before sulfur removal polishing beds.

For example, in an embodiment, once the product syngas stream reaches 400 degrees C., the products pass through a series of sintered stainless steel metal filters, such as porous metal hot filters, to remove the particulates from the gas stream. This filtering may occur at a temperature well below the ash fusion temperature (700 degrees C.-900 degrees C.), so molten ash is not a problem on the filter surface.

Other filters might be used in addition to or in place of the stainless steel metal filters. For example, high temperature fabric filter or centrifugal cyclone filters, such as multiple stage cyclone filters, might also be used. The filters might be made of material to resist 400 degrees C. The filters, e.g., the centrifugal cyclone filters, might also be coated for abrasion reduction and corrosion resistance. The filters, e.g., the centrifugal cyclone filters might be located before the sulfur remediation unit. Additionally, such a filter may allow un-reacted biomass recycling with cyclone separation, heavy cyclone stage to remove heavy particles and lighter cyclone stage to remove biomass to improve yields. Additionally, added metal oxide may allow the ash to be removed magnetically in some embodiments. Other types of filters that might also be used for ash removal include momentum change filters or abrupt changes in flow path filters, such as knock out drums. Additionally any combination of these filters might be used for ash removal.

The filters and filter housing may be cleaned, periodically, such as weekly, during nighttime shutdown operations. Cleaning methods such as CO2 blowback might be used, e.g., with CO2 recycled from the amine unit. Cleaning may keep large pressure drops from building up across the filters. Additionally, the filter can also be cleaned other ways such as physical washing, etc. The ash may be sent to an ash holding vessel, where it is staged for removal. The removed ash can be used as a soil additive, as it contains only biologically derived materials and gypsum from the sulfur removal sorbent.

At either location, the solar-driven chemical plant process may include an ash and particle storage mechanism. Such a storage mechanism may be used to store un-reacted biomass particles and ash remnants of biomass. Some example systems may store these un-reacted biomass particles and ash remnants to extract their heat. In an embodiment, a heat exchanger can be used with a bed of hot particles to recover heat for use in other places. This heat may be used to heat a working fluid, gaseous, or solid medium that drives an electricity generation apparatus or other apparatus used in doing heat based processes such as thermodynamic work, preheating water, preheating gas streams, etc.

The renewable syngas produced by the solar driven biomass gasification in the chemical reactor can be an unusually clean gas. The reason for this is the high temperature of gasification, which cracks the tar products typically found in lower temperature gasification. Sulfur compounds (primarily H2S) may be removed by reaction of the metal oxides such as CaO co-fed with the biomass. The small amount of sulfur remaining can be removed with a traditional zinc oxide bed. Particles that were in the syngas may also be removed via a filter, hot gas metal filtration, knock out drum, or other filter. The knock out drums dry out the syngas via removal of water from the gas and clean by removing light particles in the syngas. In an embodiment, gas cleanup of the solar driven syngas plant includes hot gas clean up, separation of CO2, compression, and preparation for methanol synthesis.

In an embodiment, in a final step before synthesis of methanol, the gas is passed to a compressor set. The first directly feeds between 50% and 85% (depending on time of year and time of day) of the gas to the methanol synthesis unit and brings the pressure to that required for methanol synthesis (1200 psig). The second sends the remainder of the gas to a storage unit, which reduces the required size of the methanol unit, decreases the turndown range, and improves the overall capital utilization factor of the methanol synthesis unit. The control system determines the distribution to the compressor sets based on storage planning and synthesis needs.

In an embodiment, high pressure syngas storage could be placed before the amine plant. Having the storage buffer before the amine plant may allow for amine units that can be significantly smaller. In a solar driven biorefinery, all steps preceding the high pressure syngas storage may be sized to handle peak daytime syngas flow for the location of the system. Steps following syngas storage can be sized to 53% of peak flow for site specific conditions such as southern California, Arizona, etc. latitudes.

In an embodiment, all steps preceding the high pressure syngas storage may be sized smaller because post-storage steps may be operated throughout all or part of the non-solar hours, so they do not have to process materials at peak solar levels. If too much syngas is available during the peak of the solar day, it can be stored for use during less solar rich times or for use at night.

In an embodiment, the storage may be sized about 15% larger. This can include compressors and storage electrical demand. This can be used to handle the increased volume of stored gas (as the stored gas now contains more carbon dioxide in it). The trade off is a cost optimization problem. The amine plants are generally located before the synthesis gas storage. High pressure operation may be brought on by the need for using lock hopper based biomass particle feed systems equipped with isolating valves. The system minimizes the required number of lock hopper systems per plant. This lock hopper based biomass particle feed systems is a relatively high pressure up to 75 psig feed systems.

Referring to FIG. 2, the grinding system grinds and pulverizes biomass to a particle size controlled to an average smallest dimension size between 50 microns (um) and 2000 um. These particles may have a general range of between 200 um and 1000 um. Additionally, the entrained-flow biomass feed system may supply a variety of biomass sources fed as particles into the solar driven chemical reactor. The variety includes three or more types of biomass that can be fed, individually or in combinational mixtures, from the group consisting of rice straw, corn stover, switch grass, wheat straw, miscanthus, orchard wastes, forestry wastes, energy crops, source separated green wastes and other similar biomass sources in a raw state or partially torrified state, as long as a few parameters are controlled including particle size of the biomass and operating temperature range of the reactor tubes.

In an embodiment, a feedforward and feedback control system can be configured to manage predicted changes in available solar energy as well as actual measured stochastic changes in available solar energy. The control system balances the gasification reaction between biomass feed rate and an amount of concentrated solar energy directed at the apertures or windows of the solar thermal receiver to the control temperature of the chemical reaction.

The system may control the temperature to keep the reaction temperature high enough for greater than 90 percent conversion of the biomass to product gases. The system may also control the temperature to provide for elimination of tar products to less than 200 mg/m^3 and preferably less than 50 mg/m^3. Additionally, the temperature may also be controlled to keep it at a low enough reactor tube wall temperature to not structurally weaken the walls or significantly reduce receiver efficiency. For example, a temperature of less than 1600 degrees C. might be used.

In an embodiment, the solar thermal receiver may have an indirect radiation driven geometry. For example, the indirect radiation driven geometry in the form of the cavity wall of the solar thermal receiver integrates the solar-driven chemical reactor. An inner wall of the cavity and the reactor tubes exchange energy primarily by radiation, not by convection or conduction. Exchanging energy primarily by radiation may allow for the reactor tubes to achieve a fairly uniform temperature profile even though the concentrated solar energy is merely directly impinging on the reactor tubes from one direction. Additionally, the radiation heat transfer from both the inner wall and the reactor tubes can be the primary source of energy driving the gasification reaction in which the small biomass particles act as millions of tiny absorbing surfaces of radiant heat energy coming from the inner wall and the tubes.

In an embodiment, the solar driven chemical reactor can have a downdraft geometry. Such a geometer has multiple reactor tubes in a vertical orientation. These tubes are located inside the solar thermal receiver. Additionally, the multiple reactor tubes in this chemical reactor design increase available reactor surface area for radiative exchange to the biomass particles as well as inter-tube radiation exchange. The tubes may also function to isolate a reacting environment inside the tubes from the cavity receiver environment outside the tubes. In some embodiments, high heat transfer rates of the walls and tubes allow the particles biomass to achieve the high enough temperature necessary for substantial tar destruction and complete gasification of greater than 90 percent of the biomass particles into reaction in a very short residence time between a range of 0.01 and 5 seconds.

In an embodiment of a downdraft geometry, the biomass particles fall through the downdraft reactor to substantially eliminate an undesirable build-up of product on the tube walls in the reaction zone. Buildup could lead to reduced heat transfer and even clogging of the tube because of the pressure and gravity pulling the particles through the reaction zone of the reactor tube. Additionally, low surface area to volume ratios may provide less surface area for the material to sticking. In some embodiments, ash fusion and deposition may not be a problem due to short residence time in some downdraft plant s.

The system may produce exceeding clean synthesis gas. The reaction products temperature is held high enough, temperature greater than 1000 degree C. and up to 1600 degree C. in the chemical reactor creates a greater than 90 percent conversion of the biomass particles to product gases and elimination of tar products to less than 200 mg/m^3 and preferably less than 50 mg/m^3. The CO2 removal in the CO2 removal unit, the water removal in the knockout drums, the particle filter removal in the particle filter removal component, and the sulfur removal in the syngas sulfur remediation component may provide a further clean gas. All of these contribute to a clean syngas. Additionally, this system's syngas is renewable syngas may via the greater than 90 percent conversion of the biomass particles in the solar driven biomass gasification in the chemical reactor.

In an embodiment, daily loss of sunlight requires that the amine units either be shutdown at night or operated all night at minimal liquid flow. One example proposed plant may be shut down each night. For example, each of the units can be shut down during the night. In early dawn startup may occur. The startup can be fed by stored syngas, which can bring the units online at the appropriate time.

In an embodiment, there may be times when, for reasons of manufacturability, reliability, or cost, it is best to operate one or more of the amine units around the clock even if new syngas is not being introduced. This latter case can be achieved in several ways. One example approach is with an ancillary control package that allows maintaining correct liquid levels with minimal parasitic load without the presence of flowing gas. The second operational option is the use of flowing gas by recycling the appropriate amount of post amine scrubbed syngas (with carbon dioxide effluent stream if required) in a closed loop throughout the night. When cloud events (or other unexpected short term interruptions in gas flow) threaten to exceed the dynamic range of the amine units, amine scrubbed syngas may be automatically mixed with the fresh syngas and recycled around the amine plant to maintain a required minimum flow.

Figure 5:
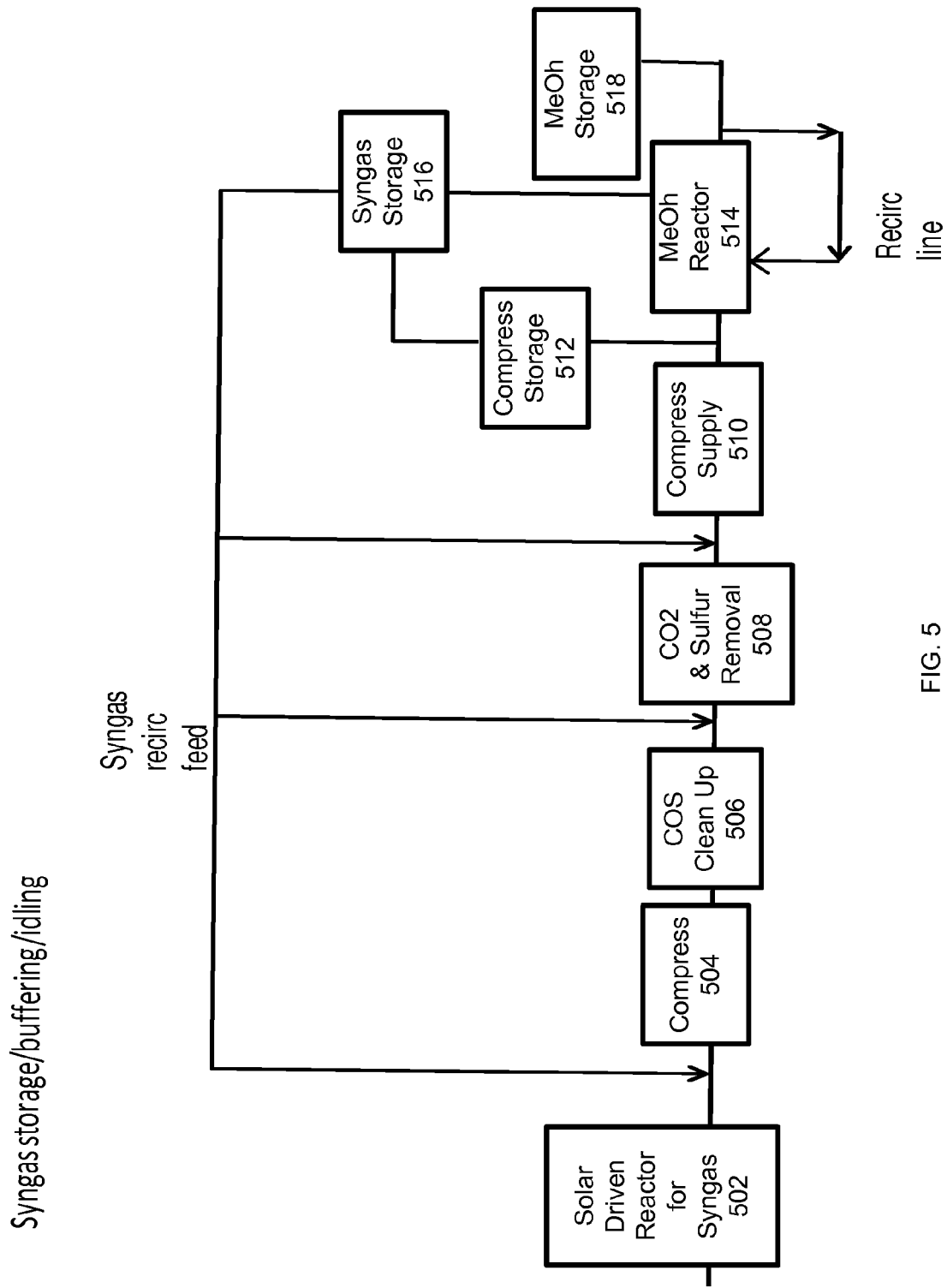
FIG. 5 illustrates a diagram of an embodiment of a compressor system.

FIG. 5 illustrates a diagram of an embodiment of a multiple sage compressor system. A compressor set pressurizes syngas in different stages in the plant. The first compressor feeds the syngas stream to the CO2 and sulfur remediation units, such as an amine plant. The pressure may be for example 100 PSIG. The second compressor directly feeds syngas to a methanol synthesis unit and brings the pressure to that required for methanol synthesis. For example, the pressure may be 750-1200 PSIG. The control system has a third compressor to send the remainder of the syngas to a storage unit. For example, the pressure may be 2000-3000 PSIG. The control system determines the distribution to the compressor sets based on storage planning and synthesis needs. Generally, the compressor will recirculate syngas from the storage tank as a way to maintain an idle state but be ready to operate 24 hours a day.

A syngas storage unit may exist to account for diurnal events placed before a CO2 and sulfur removal plant. The syngas storage buffer before the CO2 and sulfur plant allows for the CO2 and units to be significantly smaller in size/ capacity. For example, the syngas storage unit is sized to handle peak daytime syngas flow for the location of the system, whereas the CO2 and sulfur unit removes CO2 and sulfur to required levels for synthesis of methanol and may be sized for 50-85% flow. The syngas may be recirculated through these CO2 and sulfur remediation units to place the sulfur and CO2 levels in the syngas into acceptable limits. In an embodiment, the syngas storage unit is sized to operate the methanol synthesis plant for 1 hour at 100 percent peak output without receiving supplemental syngas coming out of the solar driven chemical reactor.

The synthesis gas exits the storage vessels or the syngas compressor to enter the methanol synthesis unit. The methanol synthesis unit may consist of standard shell and tube Lurgi style methanol reactors. This is a well-known process and is operated on very large scales (millions of gallons of methanol per year) worldwide. However, this methanol synthesis unit may be operated on a cyclic basis. The methanol synthesis process operates at an example 4:1 recycle ratio and converts 96% of the synthesis gas to methanol. The raw methanol is distilled from the entrained water product and fed to a standard methanol-to-gasoline (MTG) unit, where an example 97% of the methanol is converted to gasoline and LPG, with a ratio of 4.8 gallons of gasoline per gallon of LPG.

The LPG and C-2 hydrocarbons can be burned to preheat the recycle stream in the MTG plant and to generate electricity to support plant operations.

Numerous changes may occur and still be within the scope of the invention recited in the claims below.

We claim:

1. A chemical plant system, comprising:
a source of radiation;
a chemical reactor that has multiple reactor tubes located inside a thermal receiver and is in thermal communication with the source of radiation, where in the multiple reactor tubes particles of biomass are gasified in a presence of a carrier gas in a biomass gasification reaction to produce reaction products that include hydrogen and carbon monoxide gas having an exit temperature from the multiple reactor tubes exceeding at least 1000 degrees C. and the chemical reactor is primarily driven by radiation rather than by convection or conduction;
wherein the multiple reactor tubes are configured for dual functions of 1) segregating a reaction environment for the biomass gasification reaction from an atmosphere of the thermal receiver, and 2) transferring energy by the radiation, convection, and said conduction to the particles of biomass to drive an endothermic gasification reaction of the particles of biomass in the biomass gasification reaction flowing through the multiple reactor tubes;
a quench zone immediately downstream of an exit of the chemical reactor configured to immediately quench via rapid cooling of at least the hydrogen and the carbon monoxide gas of the reaction products within 10 seconds of exiting the chemical reactor to achieve a temperature after quenching of 800 degrees C. or less, which is below a level to reduce coalescence of ash remnants of the particles of biomass and stabilize formed hydrogen and carbon monoxide gas;
one or more sprayers in the quench zone configured to directly inject water or methanol into the reaction products from the multiple reactor tubes, and
a first control system programmed to control one or more of the following plant parameters to ensure the temperature is at or below 800 degrees C. when leaving the quench zone, where the first control system 1) changes a flow rate of a cooling medium being sprayed into the reaction products, and 2) provides feedback to change the flow rate of the particles of biomass into the chemical reactor, and any combination of these two;
a first on-site chemical synthesis reactor that is geographically located on a same site as the chemical reactor and integrated to receive the formed hydrogen and carbon monoxide gas of the reaction products which have passed through the quench zone, wherein the first on-site chemical synthesis reactor has an input to receive a reaction product syngas stream, which contains the formed hydrogen and carbon monoxide gas products from the chemical reactor, and then is configured to use the reaction product syngas in a hydrocarbon synthesis process to create methanol, and a second on-site chemical synthesis reactor connected downstream of the first on-site chemical synthesis reactor and configured to produce a liquid hydrocarbon fuel or other chemical; and
a compressor set, wherein a first compressor is configured to directly feed the reaction product syngas to the first on-site chemical reactor synthesis and bring pressure to that required for methanol synthesis, and a second control system is programmed to have a second compressor to send a remainder of the reaction product syngas to a storage unit, and wherein the second control system is programmed to determine a distribution to the compressor set based on storage planning and the methanol synthesis needs.

2. The chemical plant of claim 1, further comprising:
an exit of a gasification reaction zone in the multiple reactor tubes of the chemical reactor, where two or more of the multiple reactor tubes form into a group at the exit and that group combines their reaction products and un-reacted particles from the biomass gasification reaction into a portion of the quench zone; and
one or more sprayers inside the quench zone to inject the cooling medium directly into the reaction product syngas stream to make a temperature transition from the at least 1000 degrees C. to less than 500 degrees C. within 0.1-10 seconds to prevent metal dusting corrosion of walls of the multiple reactor tubes.

3. The chemical plant of claim 1, further comprising:
an exit of a gasification reaction zone in the multiple reactor tubes of the chemical reactor, where at the exit the reaction products and un-reacted particles from the biomass gasification reaction in the multiple reactor tubes are dumped into a manifold, and then into one or more syngas tubes containing the reaction product syngas stream of the reaction products and the un-reacted particles; and
one or more injection pipes in the quench zone located near the exit of the gasification reaction zone of the multiple reactor tubes, where a cooling compound consisting of at least one of 1) low temperature water (H2O), 2) methane (CH4) with the low temperature water, 3) low temperature methanol (CH3O H), and 4) various combinations is injected into the one or more syngas tubes and/or the manifold to simultaneously 1) rapidly cool the reaction product syngas stream of the reaction products from the at least 1000 degrees C. to less than 500 degrees C. and 2) provide chemical compounds necessary to achieve a proper H2 to CO ratio of the reaction product syngas stream necessary for fuel synthesis, and capture energy from heat contained in the reaction product syngas stream.

4. The chemical plant of claim 3, wherein the chemical compounds of the cooling compound necessary to achieve the proper H2 to CO ratio of the reaction product syngas stream necessary for the fuel synthesis, such as a 2:1 to 2.8:1 H2 to CO ratio, including one or more of the group consisting of:
  1) the water injected to mix with the reaction product syngas stream in order for an exothermic water gas-shift reaction to occur (CO+H2O→CO2+H2+energy) for increasing the hydrogen and decreasing the carbon monoxide,
  2) carbon dioxide supplied with natural gas used as an entrainment gas, and/or generated in the biomass gasification reaction and becomes part of the reaction product syngas stream in order for decreasing the hydrogen and increasing the carbon monoxide in an endothermic reverse water-gas shift reaction to occur (CO2+H2+energy→CO+H2O),
  3) the methane and the water are supplied and mixed with the reaction product syngas stream in the presence of a catalyst to drive an endothermic steam reformation of the methane to occur (CH4+H2O+energy→3H2+CO) for increasing an amount of hydrogen relative to the carbon monoxide,
  and the injected water is injected in a liquid state to remove more energy from the reaction product syngas stream due to an effect of a heat of vaporization on the injected cooling compound.

5. The chemical plant of claim 1, further comprising:
a heat exchanger forming part of the quench zone; and
one or more supply pipes introducing the cooling medium with the reaction products, wherein the introduced cooling medium is one or more of a tail gas of N2, CO2, low temperature syngas recycled from a storage tank, or other similar tail gas, and when the reaction products are cooled down rapidly to at least 500 degrees C., and wherein rapid quenching in the quench zone also prevents metal dusting corrosion.

6. The chemical plant of claim 1,
wherein each of the multiple reactor tubes containing unreacted products and the reaction products from the biomass gasification reaction is made of two or more sections with each section being composed of a different material able to withstand quenching conditions occurring in that section, and where another material making up a first section of each reactor tube is different than a material making up a second section of each reactor tube.

7. The chemical plant of claim 1, further comprising:
one or more cooling jackets, wherein the mutiple reactor tubes made of high temperature material that contains the reaction product syngas stream and other reaction products makes an initial transition in the quench zone to a high temperature alloy, where once the temperature of the reaction product syngas stream and other reaction products is low enough, the multiple reaction tubes carrying the reaction product syngas stream make a final transition to a low temperature material, and wherein the one or more cooling jackets cover at least a portion of the multiple reaction tubes made of either material carrying the reaction products syngas stream and other reaction products, which allows the use of the transition materials to carry the reaction product syngas stream and other reaction products downstream of the chemical reactor in the quench zone and also aids in the quenching.

8. The chemical plant of claim 2, further comprising:
an entrained-flow biomass feed system to feed the particles of biomass in the carrier gas to the multiple reactor tubes of the chemical reactor; and
a heat exchanger in the quench zone to quench and cool the reaction products exiting the multiple reactor tubes, where the heat exchanger is fed with the cooling medium, and the cooling medium carries waste heat, wherein the particles of biomass are pre-heated up to a maximum temperature of 400 degrees C. and preferably 300 degrees C. prior to entry into the chemical reactor by the carrier gas, where the carrier gas is heated by the cooling medium carrying the waste heat of the reaction products.

9. The chemical plant of claim 1, further comprising:
an entrained-flow biomass feed system to deliver the particles of biomass with a particle size controlled to an average smallest dimension size less than 2000 um; and
wherein the entrained-flow biomass feed system supplies a variety of biomass sources fed as particles into the chemical reactor, where the variety of biomass sources includes three or more types of biomass that can be fed, individually or in combinational mixtures, from the group consisting of rice straw, corn stover, switch grass, wheat straw, miscanthus, orchard wastes, energy crops, sorghum, source separated green wastes, forestry thinnings, and forestry waste in a raw state or partially torrified state, as long as a few parameters are controlled including the size of the particles of biomass and an operating temperature range of the multiple reactor tubes;
wherein the first control system balances the biomass gasification reaction between factors of a biomass feed rate and an amount of energy available from a heat source to the thermal receiver to keep a temperature at which the chemical reactor operates at 1)a high enough temperature for a greater than 90 percent conversion of the particles of biomass to produce gases and an elimination of tar products to less than 200 mg/m^3 and preferably less than 50 mg/m^3, and 2) a temperature of walls of the multiple reactor tubes less than 1600 degrees C. to not structurally weaken the walls or significantly reduce an efficiency of the thermal receiver;
wherein an indirect radiation driven geometry in the form of an inner cavity wall of the thermal receiver integrates the chemical reactor, where the inner cavity wall of the thermal receiver and the multiple reactor tubes exchange energy primarily by heat radiation, not by said convection or said conduction, allowing the multiple reactor tubes to achieve a fairly uniform temperature profile even though the energy from the heat source is merely directly impinging on the multiple reactor tubes from one direction, and wherein a radiation heat transfer from both the inner cavity wall and the multiple reactor tubes is a primary source of energy driving the gasification reaction in which the particles of biomass absorb the heat radiation coming from the inner cavity wall and the multiple reactor tubes; and
wherein the chemical reactor has a downdraft geometry with the multiple reactor tubes in a vertical orientation and located inside the thermal receiver, where the multiple reactor tubes in the chemical reactor function to increase a reactor surface area available for the radiation heat transfer to the particles of biomass and an inter-tube radiation exchange, and the multiple reactor tubes also function to isolate a reacting environment inside the multiple reactor tubes from an environment outside the multiple reactor tubes within the thermal receiver, and wherein a rate of the radiation heat transfer of the inner cavity walls and multiple reactor tubes allows the particles of biomass to achieve the high enough temperature for the elimination of the tar products to the less than 200 mg/m^3, and preferably the less than 50 mg/m^3, and the biomass gasification reaction of greater than the 90 percent conversion of the particles of biomass.

10. The chemical plant of claim 1, further comprising:
an ash and particle storage mechanism, wherein un-reacted particles of biomass and ash remnants of the particles of biomass exit the chemical reactor at the exit temperature exceeding the at least 1000 degrees C.; and
a separator that is configured to separate the un-reacted particles and the ash remnants of the particles of biomass from gas products of the reaction products into the ash and particle storage mechanism.

11. The chemical plant of claim 1, further comprising:
a sulfur removal sorbent, present in either the reaction environment for the biomass gasification reaction or initially introduced in the quench zone, to reduce an amount of sulfur present in the reaction product syngas stream exiting the quench zone; and
one or more hot particle filters to remove particulates from the reaction product syngas stream exiting the quench zone, wherein the particulates are sent to an ash holding vessel.

12. The chemical plant of claim 1, further comprising:
a sulfur remediation unit downstream of the quench zone to reduce an amount of sulfur present in the reaction product syngas stream containing said at least the hydrogen and carbon monoxide of the reaction products down to a level equal to or below 1000 ppb and preferably 50 ppb of sulfur in the reaction product syngas stream; and
multiple stage cyclone filters located before the sulfur remediation unit to allow recycling of un-reacted particles of biomass with cyclone separation, where a first heavy cyclone stage is constructed to remove heavy particles and a second lighter cyclone stage is constructed to remove lighter particles consisting mainly of the un-reacted particles of biomass, wherein a substantially particle-free syngas then passes into the sulfur remediation unit.

13. The chemical plant of claim 1, further comprising:
the one or more sprayers in the quench zone to spray a liquid cooling fluid directly into the reaction product syngas stream forming the quench zone located after the chemical reactor, where the direct spraying of the liquid cooling fluid into the reaction product syngas stream carrying the reaction products causes the liquid cooling fluid to vaporize into a superheated gas, where the one or more sprayers form the quench zone in which the temperature is brought down to 500 degrees or less;
a particle filter removal component downstream of the quench zone but upstream of a Rankine cycle engine where the ash remnants and other particles are removed from the superheated gas and the reaction products supplied from the quench zone;
where the Rankine cycle engine has an input to receive the heat radiation from the reaction products and the superheated gas, which form a medium to drive the Rankine cycle engine drawing the energy from the superheated gas and the reaction products, where the superheated gas in the reaction product stream, after transferring the energy, changes to a saturated vapor heavy in liquid content;
a $CO_2$ removal unit that sits behind the Rankine cycle engine and removes $CO_2$ content from the reaction product syngas stream supplied from the quench zone, where the $CO_2$ content of the reaction product syngas stream is reduced by the $CO_2$ removal unit to less than 15% and a preferred range of 2% -7% of the reaction product syngas stream; and
a syngas sulfur remediation component that removes sulfur gas and other sulfur compounds from the reaction product syngas stream supplied from the quench zone, where the sulfur remediation component is located after the quench zone and the particle filter removal component but before the $CO_2$ removal unit, wherein the exit temperature exceeding the at least 1000 degrees C. of the reaction products from the chemical reactor is a high enough temperature for a greater than 90 percent conversion of the particles of biomass to produce gases and elimination of tar products to less than 200 mg/m^3 and preferably less than 50 mg/m^3, and where this renewable syngas is an unusually clean gas, which is useable in a methanol synthesis plant without further filtering, and results from the greater than 90 percent conversion of the particles of biomass and being substantially tar free, having $CO_2$ removal in the $CO_2$ removal unit, having particle filter removal in the particle filter removal component, and having sulfur removal in the syngas sulfur remediation component.

14. The chemical plant of claim 1, further comprising:
one or more supply lines to co-feed sorbent metal oxide particles with the particles biomass that pass through the multiple reactor tubes during the biomass gasification reaction to remove sulfur from the reaction products coming out with an effluent reaction product syngas stream, wherein the co-fed sorbent metal oxide particles removing the sulfur during the biomass gasification reaction include one or more from a group consisting of lime (CaO), zinc oxide (ZnO), and magnesium oxide ($Mn_3O_4$).

15. The chemical plant of claim 1, further comprising:
one or more supply lines to co-feed sorbent zinc oxide particles with the reaction products from the chemical reactor into the quench zone, wherein the co-fed zinc oxide particles are selected to be most effective in sulfur removal in a temperature range of 700-900 degrees C. range and remove sulfur from the reaction products entering the quench zone to a level equal to or below 100 parts per million (ppm) and preferably 10 ppm of sulfur in gaseous components of the reaction product syngas stream exiting the quench zone.

16. The chemical plant of claim 1, further comprising:
one or more sulfur removal beds containing a metal oxide such as ZnO or $CaSO_4$ sorbents, and the one or more sulfur removal beds take a concentration of $H_2S$ down to levels below 1000 parts per billion (ppb) and preferably 50 ppb, wherein the metal oxide effectively traps sulfur, and wherein the one or more sulfur removal beds are placed before a $CO_2$ removal treatment plant.

* * * * *